(12) United States Patent
Ihara et al.

(10) Patent No.: US 7,301,032 B2
(45) Date of Patent: Nov. 27, 2007

(54) 1,2,4-THIADIAZOLE COMPOUNDS AND ARTHROPOD CONTROLLING COMPOSITION CONTAINING THE SAME

(75) Inventors: Hideki Ihara, Osaka (JP); Daisuke Takaoka, Osaka (JP)

(73) Assignee: Sumitomo Chemical Company Limited, Tokyo (JP)

( * ) Notice: Subject to any disclaimer, the term of this patent is extended or adjusted under 35 U.S.C. 154(b) by 223 days.

(21) Appl. No.: 10/532,478

(22) PCT Filed: Oct. 28, 2003

(86) PCT No.: PCT/JP03/13750

§ 371 (c)(1),
(2), (4) Date: Apr. 22, 2005

(87) PCT Pub. No.: WO2004/046125

PCT Pub. Date: Jun. 3, 2004

(65) Prior Publication Data

US 2006/0052422 A1    Mar. 9, 2006

(30) Foreign Application Priority Data

Nov. 21, 2002 (JP) .............................. 2002-337884

(51) Int. Cl.
*C07D 285/08* (2006.01)
*A01N 43/82* (2006.01)
*A01N 43/836* (2006.01)

(52) U.S. Cl. ...................................... 548/129; 514/361
(58) Field of Classification Search ................ 514/362; 548/129
See application file for complete search history.

(56) References Cited

FOREIGN PATENT DOCUMENTS

| DE | 30 30 661 A1 | 4/1982 |
|----|--------------|--------|
| EP | 0 273 534 A2 | 12/1987 |
| EP | 0 410 551 A1 | 1/1991 |
| EP | 1 475 374 A1 | 11/2004 |

OTHER PUBLICATIONS

Merriam-Webster OnLine Dictionary, definition of the term arthropod.*
Encyclopaedia Britannica, meaning of the term arthropod.*

* cited by examiner

*Primary Examiner*—Johann R. Richter
*Assistant Examiner*—Nathan W. Schlientz
(74) *Attorney, Agent, or Firm*—Akin Gump Strauss Hauer & Feld LLP

(57) ABSTRACT

The present invention relates to a novel 1,2,4-thiadiazole compound represented by the formula (1):

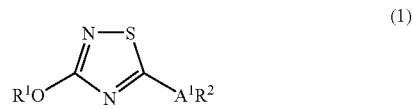

wherein, $R^1$ represents C3-C7 alkynyl that may be substituted with halogen atom; $R^2$ represents C3-C8 cycloalkyl which may be substituted with C1-C4 alkyl, halogen atom and trifluoromethyl or the like; $A^1$ represents a single bond, C1-C2 alkylene or C2-C3 alkylidene.

The 1,2,4-thiadiazole compound has an excellent arthropod controlling activity, and can effectively control an arthropod pests such as insect pests, acarine pests and the like.

16 Claims, No Drawings

1,2,4-THIADIAZOLE COMPOUNDS AND ARTHROPOD CONTROLLING COMPOSITION CONTAINING THE SAME

CROSS-REFERENCE TO RELATED APPLICATION

This application is a section 371 of International Application No. PCT/JP2003/013750, filed Oct. 28, 2003, which was published in the English language on Jun. 3, 2004, under International Publication No. WO 2004/046125 A1 and the disclosure of which is incorporated herein by reference.

TECHNICAL FIELD

The present invention relates to 1,2,4-thiadiazole compounds and arthropod controlling composition containing the same.

BACKGROUND ART

While various pesticide compositions have been used for the purpose of controlling arthropod pests such as insect pests, acarine pests and the like, sometimes the effect of those pesticide compositions is not always enough, and therefore the development of novel arthropod controlling compositions having enough effect is desired.

It is an objective of the present invention to provide novel compounds having a arthropod controlling effect, arthropod controlling compositions containing the same compounds, and methods for controlling arthropods applying effective dose of the same compounds to pests or their habitat.

BRIEF SUMMARY OF THE INVENTION

The present inventors have intensively studied to find compounds having excellent arthropod controlling activity, and as a result, found out that the 1,2,4-thiadiazole compounds of formula (1) as depicted below have an excellent controlling activity for arthropod pests such as insect pests and acarine pests, thereby completing the present invention.

Namely, the present invention relates to a 1,2,4-thiadiazole compound represented by the formula (1) (hereinafter referred to as the present invention compound(s)):

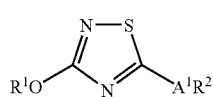

(1)

wherein, $R^1$ represents C3-C7 alkynyl that may be substituted with halogen atom; $R^2$ represents C3-C8 cycloalkyl, C5-C8 cycloalkenyl or C7-C11 bicycloalkyl, wherein the C3-C8 cycloalkyl, the C5-C8 cycloalkenyl and the C7-C11 bicycloalkyl may be substituted with a substituent(s) selected from a group of C1-C4 alkyl, halogen atom and trifluoromethyl; $A^1$ represents a single bond, C1-C2 alkylene or C2-C3 alkylidene;

an arthropod controlling composition containing the present invention compound as active ingredient; and a method for controlling arthropod pests comprising applying an effective dose of the present invention compound to arthropod pests or habitat of arthropod pests.

DETAILED DESCRIPTION OF THE INVENTION

In the present invention, the following groups are exemplified as each substituent described above.

The C3-C7 alkynyl that may be substituted with halogen atom represented by $R^1$ includes, for example, 2-propynyl, 2-butynyl, 4-fluoro-2-butynyl, 3-butynyl, 1-methyl-2-butynyl, 2-pentynyl, 3-pentynyl, 4,4-dimethyl-2-pentynyl, 3-chloro-2-propynyl, 3-bromo-2-propynyl, 3-iodo-2-propynyl and 1-methyl-2-propynyl.

In the C3-C8 cycloalkyl, the C5-C8 cycloalkenyl and C7-C11 bicycloalkyl represented by $R^2$, C1 to C4 alkyl as substituents includes, for example, methyl, ethyl, propyl, isopropyl and 1,1-dimethylethyl.

The C3-C8 cycloalkyl that may be substituted with a substituent(s) selected from a group of C1-C4 alkyl, halogen atom and trifluoromethyl represented by $R^2$ includes, for example, cyclobutyl, cyclopentyl, 2-methylcyclopentyl, 3-methylcyclopentyl, 2-ethylcyclopentyl, 3-ethylcyclopentyl, 2,5-dimethylcyclopentyl, 3,4-dimethylcyclopentyl, cyclohexyl, 2-methylcyclohexyl, 3-methylcyclohexyl, 4-methylcyclohexyl, 2-ethylcyclohexyl, 3-ethylcyclohexyl, 4-ethylcyclohexyl, 2-propylcyclohexyl, 3-propylcyclohexyl, 4-propylcyclohexyl, 3-isopropylcyclohexyl, 3,3-dimethylcyclohexyl, 3,5-dimethylcyclohexyl, 3,5-diethylcyclohexyl, 4,4-dimethylcyclohexyl, 3,3,5,5-tetramethylcyclohexyl, 3-fluorocyclohexyl, 3-chlorocyclohexyl, 3-bromocyclohexyl, 3-trifluoromethylcyclohexyl, 3,5-difluorocyclohexyl, 3,5-dichlorocyclohexyl, 3,5-dibromocyclohexyl, 3,5-bis(trifluoromethyl)cyclohexyl, 1-chlorocyclohexyl, 1-bromocyclohexyl, 1-chloro-3-methylcyclohexyl, 1-bromo-3-methylcyclohexyl, 1-chloro-3,5-dimethylcyclohexyl, 1-bromo-3,5-dimethylcyclohexyl, cycloheptyl, 2-methylcycloheptyl, 3-methylcycloheptyl, and cyclooctyl.

The C5-C8 cycloalkenyl that may be substituted with a substituent(s) selected from a group of C1-C4 alkyl, halogen atom and trifluoromethyl represented by $R^2$ includes, for example, 1-cyclopentenyl, 2-methyl-1-cyclopentenyl, 3-methyl-1-cyclopenteny, 4-methyl-1-cyclopentenyl, 5-methyl-1-cyclopentenyl, 2-cyclopentenyl, 2-methyl-2-cyclopentenyl, 3-methyl-2-cyclopentenyl, 4-methyl-2-cyclopentenyl, 5-methyl-2-cyclopentenyl, 3-cyclopentenyl, 2-methyl-3-cyclopentenyl, 3-methyl-3-cyclopentenyl, 4-methyl-3-cyclopentenyl, 5-methyl-3-cyclopentenyl, 1-cyclohexenyl, 2-methyl-1-cyclohexenyl, 3-methyl-1-cyclohexenyl, 4-methyl-1-cyclohexenyl, 5-methyl-1-cyclohexenyl, 6-methyl-1-cyclohexenyl, 2-cyclohexenyl, 2-methyl-2-cyclohexenyl, 3-methyl-2-cyclohexenyl, 4-methyl-2-cyclohexenyl, 5-methyl-2-cyclohexenyl, 6-methyl-2-cyclohexenyl, 3-cyclohexenyl, 2-methyl-3-cyclohexenyl, 3-methyl-3-cyclohexenyl, 4-methyl-3-cyclohexenyl, 5-methyl-3-cyclohexenyl, 6-methyl-3-cyclohexenyl, 1-cycloheptenyl, 2-cycloheptenyl, 3-cycloheptenyl, 1-cyclooctenyl, 2-cyclooctenyl, 3-cyclooctenyl and 4-cyclooctenyl.

The C7-C11 bicycloalkyl that may be substituted with a substituent(s) selected from a group of C1-C4 alkyl, halogen atom and trifluoromethyl represented by $R^2$ includes, for example, bicyclo[2.2.1]-2-heptyl, 7,7-dimethylbicyclo[2.2.1]-2-heptyl, bicyclo[2.2.1]-7-heptyl, bicyclo[2.2.2]-2-octyl, bicyclo[3.2.1]-2-octyl, cis-bicyclo[4.4.0]-2-decanyl and trans-bicyclo[4.4.0]-2-decanyl.

The C1-C2 alkylene represented by $A^1$ is methylene (—$CH_2$—) or ethylene (—$CH_2CH_2$—); the C2-C3 alkylidene represented by $A^1$ is ethylidene (—CH($CH_3$)—), propylidene (—CH($CH_2CH_3$))- or isopropylidene (—C($CH_3$)$_2$—).

As the aspects of the present invention compound, for example, the following compounds are exemplified.

a 1,2,4-thiadiazole compound wherein $R^1$ is 2-butynyl in the formula (1);

a 1,2,4-thiadiazole compound wherein $R^1$ is 2-pentynyl in the formula (1);

a 1,2,4-thiadiazole compound wherein $R^2$ is cyclopentyl that may be substituted with C1-C4 alkyl in the formula (1);

a 1,2,4-thiadiazole compound wherein $R^2$ is cyclohexyl that may be substituted with C1-C4 alkyl in the formula (1);

a 1,2,4-thiadiazole compound wherein $A^1$ is single bond in the formula (1);

a 1,2,4-thiadiazole compound wherein $A^1$ is methylene in the formula (1);

a 1,2,4-thiadiazole compound wherein $R^1$ is 2-butynyl and $R^2$ is cyclopentyl that may be substituted with C1-C4 alkyl in the formula (1);

a 1,2,4-thiadiazole compound wherein $R^1$ is 2-butynyl and $R^2$ is cyclohexyl that may be substituted with C1-C4 alkyl in the formula (1);

a 1,2,4-thiadiazole compound wherein $R^1$ is 2-pentynyl and $R^2$ is cyclopentyl that may be substituted with C1-C4 alkyl in the formula (1);

a 1,2,4-thiadiazole compound wherein $R^1$ is 2-pentynyl and $R^2$ is cyclohexyl that may be substituted with C1-C4 alkyl in the formula (1);

a 1,2,4-thiadiazole compound wherein $R^1$ is 2-butynyl and $A^1$ is single bond that may be substituted with C1-C4 alkyl in the formula (1); a 1,2,4-thiadiazole compound wherein $R^1$ is 2-butynyl and $A^1$ is methylene that may be substituted with C1-C4 alkyl in the formula (1);

a 1,2,4-thiadiazole compound wherein $R^1$ is 2-pentynyl and $A^1$ is single bond that may be substituted with C1-C4 alkyl in the formula (1);

a 1,2,4-thiadiazole compound wherein $R^1$ is 2-pentynyl and $A^1$ is methylene that may be substituted with C1-C4 alkyl in the formula (1);

a 1,2,4-thiadiazole compound wherein $R^2$ is cyclopentyl that may be substituted with C1-C4 alkyl and $A^1$ is single bond in the formula (1);

a 1,2,4-thiadiazole compound wherein $R^2$ is cyclopentyl that may be substituted with C1-C4 alkyl and $A^1$ is methylene in the formula (1);

a 1,2,4-thiadiazole compound wherein $R^2$ is cyclohexyl that may be substituted with C1-C4 alkyl and $A^1$ is single bond in the formula (1);

a 1,2,4-thiadiazole compound wherein $R^2$ is cyclohexyl that may be substituted with C1-C4 alkyl and $A^1$ is methylene in the formula (1);

a 1,2,4-thiadiazole compound wherein $R^1$ is 2-butynyl, $R^2$ is cyclopentyl that may be substituted with C1-C4 alkyl and $A^1$ is single bond in the formula (1);

a 1,2,4-thiadiazole compound wherein $R^1$ is 2-butynyl, $R^2$ is cyclohexyl that may be substituted with C1-C4 alkyl and $A^1$ is single bond in the formula (1);

a 1,2,4-thiadiazole compound wherein $R^1$ is 2-pentynyl, $R^2$ is cyclopentyl that may be substituted with C1-C4 alkyl and $A^1$ is single bond in the formula (1);

a 1,2,4-thiadiazole compound wherein $R^1$ is 2-pentynyl, $R^2$ is cyclohexyl that may be substituted with C1-C4 alkyl and $A^1$ is single bond in the formula (1);

a 1,2,4-thiadiazole compound wherein $R^1$ is 2-butynyl, $R^2$ is cyclohexyl that may be substituted with C1-C4 alkyl and $A^1$ is methylene in the formula (1);

a 1,2,4-thiadiazole compound wherein $R^1$ is 2-butynyl, $R^2$ is cyclohexyl that may be substituted with C1-C4 alkyl and $A^1$ is methylene in the formula (1);

a 1,2,4-thiadiazole compound wherein $R^1$ is 2-pentynyl, $R^2$ is cyclopentyl that may be substituted with C1-C4 alkyl and $A^1$ is methylene in the formula (1);

a 1,2,4-thiadiazole compound wherein $R^1$ is 2-pentynyl, $R^2$ is cyclohexyl that may be substituted with C1-C4 alkyl and $A^1$ is methylene in the formula (1).

The following will describe a production process for the present invention compounds.

The present invention compounds can be produced, for example, by reacting a sulfone compound (2) and an alcohol compound (5);

wherein $R^1$, $R^2$ and $A^1$ are as defined above.

The reaction is generally carried out in the presence of base in a solvent.

The solvent to be used in the reaction includes, for example, ethers such as 1,2-dimethoxyethane, 1,4-dioxane, tetrahydrofuran and the like, acid amides such as N,N-dimethylformamide and the like, and mixtures thereof.

The base to be used in the reaction includes, for example, inorganic base such as sodium hydride, potassium carbonate and the like.

The amount of the base to be used in the reaction is usually 1 to 2 moles, and the amount of the alcohol compound (5) is usually 1 to 1.5 moles; relative to 1 mole of the sulfone compound (2).

The reaction temperature is usually in the range of −20° C. to 80° C., and the reaction time is usually in the range of 1 to 24 hours.

After completion of the reaction, the present invention compound can be isolated by subjecting the reaction mixture to ordinary post-treatment such as adding the reaction mixture into water, extracting with an organic solvent, concentrating the organic phase obtained and the like. The isolated present invention compound can be purified by a technique such as chromatography and the like, if necessary.

The sulfone compound (2) can be produced by reacting a sulfide compound (3) and an oxidizing agent;

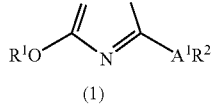

wherein $R^2$ and $A^1$ are as defined above.

The reaction is generally carried out in a solvent.

The solvent to be used in the reaction includes, for example, halogenated hydrocarbons such as chloroform, dichloromethane and the like.

The oxidizing agent to be used in the reaction includes, for example, peroxyacetic acid, 3-chloroperoxybezoic acid and the like.

The amount of the oxidizing agent to be used in the reaction is usually 2 to 2.5 moles relative to 1 mole of the sulfide compound (3).

The reaction temperature is usually in the range of −20° C. to 60° C., and the reaction time is usually in the range of 1 to 24 hours.

After completion of the reaction, the sulfone compound (2) can be isolated by subjecting the reaction mixture to ordinary post-treatment such as adding the reaction mixture into aqueous solution of sodium hydrogensulfite, extracting with an organic solvent, concentrating the organic phase obtained and the like. The isolated sulfone compound (2) can be purified by a technique such as chromatography and the like, if necessary.

The sulfide compound (3) can be produced by reacting 5-chloro-3-methylthio-1,2,4-thiadiazole and an organozinc compound (4) in the presence of transition metal catalyst;

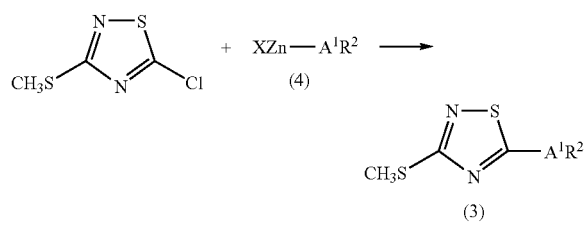

wherein $R^2$ and $A^1$ are as defined above, and X represents bromine atom or iodine atom.

The reaction is generally carried out under atmosphere of inactive gas such as nitrogen and argon, in a solvent.

The solvent to be used in the reaction includes, for example, ethers such as 1,2-dimethoxyethane, 1,4-dioxane, tetrahydrofuran and the like, aromatic hydrocarbon such as benzene, toluene and the like.

The transition metal catalyst to be used in the reaction includes, for example, palladium catalyst such as palladium (II) acetate, tetrakis(triphenylphosphine) palladium(0), {1,1'-bis(diphenylphosphino)ferrocene} dichloro palladium (II) dichloromethane complex and bis(triphenylphosphine) palladium(II) chloride.

The amount of the transition metal catalyst is usually 0.001 to 0.1 mole, and the amount of the organozinc compound (4) is usually 0.9 to 1.5 moles; relative to 1 mole of 5-chloro-3-methylthio-1,2,4-thiadiazole.

The reaction temperature is usually in the range of 0 to 150° C., and the reaction time is usually in the range of 1 to 24 hours.

After completion of the reaction, the sulfide compound (3) can be isolated by subjection the reaction mixture to ordinary post-treatment such as concentrating the reaction mixture as such, subjecting the residue to the chromatography and the like.

The organozinc compound (4) can be produced by reacting a halogenated compound represented with $R^2A^1$-X and metal zinc.

A part of the present invention compounds can be produced by a following method.

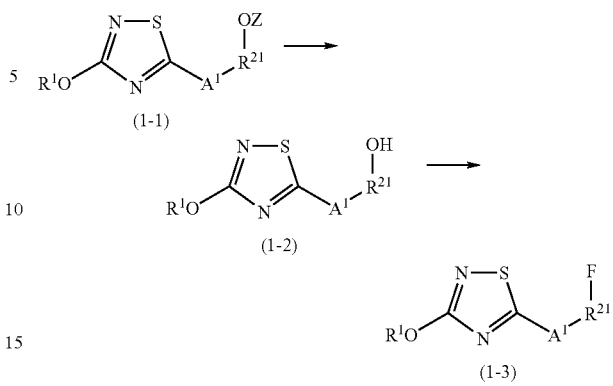

wherein $R^1$ and $A^1$ are as defined above, Z represents a protecting group of hydroxy such as methoxymethyl, and $R^{21}$ represents C3-C8 cycloalkandiyl that may be substituted C1-C4 alkyl, C5-C8 cycloalkendiyl that may be substituted C1-C4 alkyl or C7-C11 bicycloalkandiyl that may be substituted C1-C4 alkyl.

The compound (1-2) can be produced by deprotecting of the protecting group of hydroxy of the compound (1-1). In a case of the protecting group represented by Z is methoxymethyl, for example, it can be produced by reacting with water in the presence of acid. The acid to be used in the reaction includes, for example, hydrochloric acid, sulfuric acid and para-toluenesulfonic acid.

The compound (1-3) can be produced by reacting the compound (1-2) and a fluorination reagent. The fluorination reagent to be used includes, for example, diethylaminosulfur trifluoride.

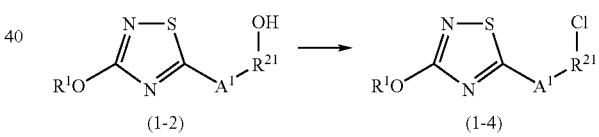

wherein $R^1$, $A^1$ and $R^{21}$ are defined above.

The compound (1-4) can be produced by reacting the compound (1-2) in the presence of triphenylphosphine and carbon tetrachloride.

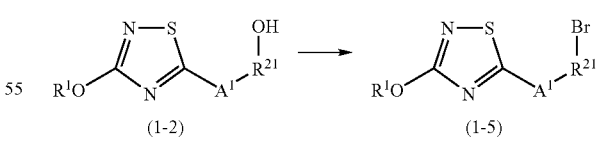

wherein $R^1$, $A^1$, Z and $R^{21}$ are defined above.

The compound (1-5) can be produced by reacting the compound (1-2) and a bromination reagent. The bromination reagent to be used includes, for example, triphenylphosphine bromide.

The examples of the present invention compound, which can be produced according to the above-described production processes, are listed below.

A 1,2,4-thiadiazole compound (from I.01.01 to I.01.89) wherein $R^1$ is 2-propynyl, $A^1$ is single bond and $R^2$ is a substituent selected from the group described below in the formula (1);

a 1,2,4-thiadiazole compound (from I.02.01 to I.02.89) wherein $R^1$ is 2-butynyl, $A^1$ is single bond and $R^2$ is a substituent selected from the group described below in the formula (1);

a 1,2,4-thiadiazole compound (from I.03.01 to I.03.89) wherein $R^1$ is 1-methyl-2-butynyl, $A^1$ is single bond and $R^2$ is a substituent selected from the group described below in the formula (1);

a 1,2,4-thiadiazole compound (from I.04.01 to I.04.89) wherein $R^1$ is 2-pentynyl, $A^1$ is single bond and $R^2$ is a substituent selected from the group described below in the formula (1);

a 1,2,4-thiadiazole compound (from I.05.01 to I.05.89) wherein $R^1$ is 2-butynyl, $A^1$ is methylene and $R^2$ is a substituent selected from the group described below in the formula (1);

a 1,2,4-thiadiazole compound (from I.06.01 to I.06.89) wherein $R^1$ is 1-methyl-2-butynyl, $A^1$ is single bond and $R^2$ is a substituent selected from the group described below in the formula (1);

a 1,2,4-thiadiazole compound (from I.07.01 to I.07.89) wherein $R^1$ is 2-pentynyl, $A^1$ is single bond and $R^2$ is a substituent selected from the group described below in the formula (1).

cyclobutyl(01), cyclopentyl(02), 2-methylcyclopentyl(03), 3-methylcyclopentyl(04), 2-ethylcyclopentyl(05), 3-ethylcyclopentyl(06), 2,5-dimethylcyclopentyl(07), 3,4-dimethylcyclopentyl(08), cyclohexyl(09), 2-methylcyclohexyl(10), 3-methylcyclohexyl(11), 4-methylcyclohexyl(12), 2-ethylcyclohexyl(13), 3-ethylcyclohexyl(14), 4-ethylcyclohexyl(15), 2-propylcyclohexyl(16), 3-propylcyclohexyl(17), 4-propylcyclohexyl(18), 3-isopropylcyclohexyl(19), 3,3-dimethylcyclohexyl(20), 3,5-dimethylcyclohexyl(21), 3,5-diethylcyclohexyl(22), 4,4-dimethylcyclohexyl(23), 3,3,5,5-tetramethylcyclohexyl(24), 3-fluorocyclohexyl(25), 3-chlorocyclohexyl(26), 3-bromocyclohexyl(27), 3-trifluoromethylcyclohexyl(28), 3,5-difluorocyclohexyl(29), 3,5-dichlorocyclohexyl(30), 3,5-dibromocyclohexyl(31), 3,5-bis(trifluoromethyl)cyclohexyl(32), 1-chlorocyclohexyl(33), 1-bromocyclohexyl(34), 1-chloro-3-methylcyclohexyl(35), 1-bromo-3-methylcyclohexyl(36), 1-chloro-3,5-dimethylcyclohexyl(37), 1-bromo-3,5-dimethylcyclohexyl(38), cycloheptyl(39), 2-methylcycloheptyl(40), 3-methylcycloheptyl(41), cyclooctyl(42), 1-cyclopentenyl(43), 2-methyl-1-cyclopentenyl(44), 3-methyl-1-cyclopenteny(45), 4-methyl-1-cyclopentenyl(46), 5-methyl-1-cyclopentenyl(47), 2-cyclopentenyl(48), 2-methyl-2-cyclopentenyl(49), 3-methyl-2-cyclopentenyl(50), 4-methyl-2-cyclopentenyl(51), 5-methyl-2-cyclopentenyl(52), 3-cyclopentenyl(53), 2-methyl-3-cyclopentenyl(54), 3-methyl-3-cyclopentenyl(55), 4-methyl-3-cyclopentenyl(56), 5-methyl-3-cyclopentenyl(57), 1-cyclohexenyl(58), 2-methyl-1-cyclohexenyl(59), 3-methyl-1-cyclohexenyl(60), 4-methyl-1-cyclohexenyl(61), 5-methyl-1-cyclohexenyl(62), 6-methyl-1-cyclohexenyl(63), 2-cyclohexenyl(64), 2-methyl-2-cyclohexenyl(65), 3-methyl-2-cyclohexenyl(66), 4-methyl-2-cyclohexenyl(67), 5-methyl-2-cyclohexenyl(68), 6-methyl-2-cyclohexenyl(69), 3-cyclohexenyl(70), 2-methyl-3-cyclohexenyl(71), 3-methyl-3-cyclohexenyl(72), 4-methyl-3-cyclohexenyl(73), 5-methyl-3-cyclohexenyl(74), 6-methyl-3-cyclohexenyl(75), 1-cycloheptenyl(76), 2-cycloheptenyl(77), 3-cycloheptenyl(78), 1-cyclooctenyl(79), 2-cyclooctenyl(80), 3-cyclooctenyl(81), 4-cyclooctenyl(82), bicyclo[2.2.1]-2-heptyl(83), 7,7-dimethylbicyclo[2.2.1]-2-heptyl(84), bicyclo[2.2.1]-7-heptyl(85), bicyclo[2.2.2]-2-octyl(86), bicyclo[3.2.1]-2-octyl(87), cis-bicyclo[4.4.0]-2-decanyl(88) and trans-bicyclo[4.4.0]-2-decanyl.(89).

The arthropod pests against which the present invention compound has control activity may include, for example, insect pests and acarine pests. Specific examples are listed below:

Hemiptera: Delphacidae such as *Laodelphax striatellus*, *Nilaparvata lugens*, and *Sogatella furcifera*; Deltocephalidae such as *Nephotettix cincticeps* and *Empoasca onukii*; Aphididae such as *Aphis gossypii* and *Myzus persicae*; Pentatomidae; Aleyrodidae such as *Trialeurodes vaporariorum, Bemisia tabaci*, and *Bemisia argentifolii; Coccidae*; Tingidae; Psyllidae;

Lepidoptera: Pyralidae such as *Chilo suppressalis, Cnaphalocrocis medinalis, Ostrinia nubilalis*, and *Parapediasia teterrella*; Noctuidae such as *Spodoptera litura, Spodoptera exigua, Pseudaletia separata, Mamestra brassicae, Agrotis ipsilon, Thoricoplusia* spp., *Heliothis* spp., *Helicoverpa* spp., and *Earias* spp.; Pieridae such as *Pieris rapae crucivora*; Tortricidae such as *Adoxophyes orana fasciata, Grapholita molesta*, and *Cydia pomonella*; Carposinidae such as *Carposina niponensis*; Lyonetiidae such as *Lyonetia clerkella*; Gracillariidae such as *Phyllonorycter ringoniella*; Phyllocnistidae such as *Phyllocnistis citrella*; Yponomeutidae such as *Plutela xylostella*; Gelechiidae such as *Pectinophora gossypiella*; Arctiidae; Tineidae;

Diptera: Calicidae such as *Culex pipiens* pallens, *Culex tritaeniorhynchus*, and *Culex quinquefasciatus; Aedes* spp. such as *Aedes aegypti* and *Aedes alhopictus; Anopheles* spp. such as *Anopheles sinensis*; Chironomidae; Muscidae such as *Musca domestica* and *Muscina stabulans*; Calliphoridae; Sarcophagidae; Fanniidae; Anthomyiidae such as *Delia platura* and *Delia antiqua*; Tephritidae; Drosophilidae; Psychodidae; Tabanidae; Simuliidae; Stomoxyidae; Agromyzidae;

Coleoptera: *Diabrotica* spp. such as *Diabrotica virgifera virgifera* and *Diabrotica undecimpunctata howardi*; Scarabaeidae such as *Anomala cuprea* and *Anomala rufocuprea*; Curculionidae such as *Sitophilus zeamais, Lissorhoptrus oryzophilus*, and *Callosobruchuys chienensis*; Tenebrionidae such as *Tenebrio molitor* and *Tribolium castaneum; Chrysomelidae* such as *Oulema oryzae, Aulacophora femoralis, Phyllotreta striolata*, and *Leptinotarsa decemlineata*; Anobiidae; *Epilachna* spp. such as *Epilachna vigintioctopunctata*; Lyctidae; Bostrychidae; Cerambycidae; *Paederus fuscipes;*

Thysanoptera: *Thripidae* spp. including *Thrips* spp. such as *Thrips palmi, Frankliniella* spp. such as *Frankliniella occidentalis*, and *Sciltothrips* spp. such as *Sciltothrips dorsalis; Phlaeothripidae* spp.;

Hymenoptera: Tenthredinidae; Formicidae; Vespidae;

Dictyoptera: *Periplaneta* spp.; *Blatta* spp.;

Orthoptera: Acrididae; Gryllotalpidae; Aphaniptera: *Pulex irritans*;

Anoplura: *Pediculus humanus*;

Isoptera: Termitidae;

Acarina: Tetranychidae.

The arthropod controlling composition of the present invention contains the present invention compound and an inert carrier. Generally, it is a preparation obtained by mixing the present invention compound and a carrier such as a solid carrier, a liquid carrier and a gaseous carrier, and if necessary, adding a surfactant and other adjuvant for formulation. The formulation includes, for example, an emulsion, an oil solution, a shampoo formulation, a flowable formulation, a powder, a wettable powder, a granule, a paste formulation, a microcapsule, a foam, an aerosol, a carbon dioxide gas formulation, a tablet, a resin formulation and the like. These formulations can be converted to use into a poison bait, a pesticide coil, an electric pesticide mat, a smoking agent, a fumigant or sheet.

In the pesticide composition of the present invention, the present invention compound is usually contained in an amount of 0.1% to 95% by weight.

The solid carrier for formulation includes, for example, a fine power and a granule of clays (e.g., kaolin clay, diatomite, bentonite, Fubasami clay, acid clay, etc.), synthetic hydrated silicon oxide, talc, ceramic, other inorganic minerals (e.g., sericite, quartz, sulfur, activated carbon, calcium carbonate, hydrated silica) or chemical fertilizers (e.g., ammonium sulfate, ammonium phosphate, ammonium nitrate, ammonium chloride, urea).

The liquid carrier for formulation includes, for example, aromatic or aliphatic hydrocarbons (e.g., xylene, toluene, alkylnaphthalene, phenylxylylethane, kerosine, light oil, hexane, cyclohexane), halogenated hydrocarbons (e.g., chlorobenzene, dichloromethane, dichloroethane, trichloroethane), alcohols (e.g., methanol, ethanol, isopropyl alcohol, butanol, hexanol, ethylene glycol), ethers (e.g., diethyl ether, ethylene glycol dimethyl ether, diethylene glycol monomethyl ether, diethylene glycol monoethyl ether, propylene glycol monomethyl ether, tetrahydrofuran, dioxane), esters (e.g., ethyl acetate, butyl acetate), ketones (e.g., acetone, methyl ethyl ketone, methyl isobutyl ketone, cyclohexanone), nitriles (e.g., acetonitrile, isobutyronitrile), sulfoxides (e.g., dimethylsulfoxide), acid amides (e.g., N,N-dimethylformamide, N,N-dimethylacetamide), vegetable oils (e.g., soy bean oil, cotton seed oil), vegetable essential oils (e.g., orange oil, hyssop oil, lemon oil) and water.

The gaseous carrier for formulation includes, for example, butane gas, chlorofluorocarbons, liquefied petroleum gas (LPG), dimethyl ether, carbon dioxide and the like.

The surfactant for formulation includes, for example, alkyl sulfate salts, alkylsulfonic acid salts, alkylarylsulfonic acid salts, alkyl aryl ethers and their polyoxyethylene derivatives, polyethylene glycol ethers, polyhydric alcohol esters, and sugar alcohol derivatives.

The other adjuvant for formulation includes, for example, binders, dispersants and stabilizers, and specifically for example, casein, gelatin, polysaccharides (e.g., starch, gum arabic, cellulose derivatives, alginic acid), lignin derivatives, bentonite, sugars, synthetic water-soluble polymers (e.g., polyvinyl alcohol, polyvinylpyrrolidone, polyacrylic acid), PAP (isopropyl acid phosphate), BHT (2,6-di-t-butyl-4-methylphenol), BHA (a mixture of 2-t-butyl-4-methoxyphenol and 3-t-butyl-4-methoxyphenol), vegetable oils, mineral oils, fatty acids, and fatty acid esters.

A base for the poison bait includes, for example, grain powders, vegetable oils, sugars, and crystalline cellulose, and further, if necessary, antioxidants such as dibutylhydroxytoluene and nordihydroguaiaretic acid, preservatives such as dehydroacetic acid, agents for preventing children and pets from erroneously eating such as hot pepper powder, and pest-attractive flavors such as cheese flavor, onion flavor and peanut oil may be added to the base.

Arthropod pests can be controlled by applying an effective dose of the present invention compound to pests directly and/or habitats of pests (e.g., nest, plant, soil). Usually the preparation of the pesticide composition of the present invention is used as the present invention compound.

When the pesticide composition of the present invention is used for a control of pests in agriculture and forestry, the application amount is usually 0.1 to 1,000 g as an active ingredient per 1000 m$^2$. The emulsions, wettable powders, flowables and microcapsule formulations are usually applied after dilution with water to have an active ingredient concentration of 0.01 to 10000 ppm, while oil solution, powders and granules are usually applied as such. These preparations may be sprayed directly to the plant to be protected from pests. The pests living in a soil can be controlled by treating the soil with these preparations, and the preparations can also be applied to treat seedbeds prior to the planting plants or to treat planting holes or plant bottoms in the planting. Furthermore, the sheet preparation of the pesticide composition of the present invention can be applied by a method such as winding around plants, stretching in the vicinity of plants and laying on the soil surface at the plant bottom.

When the pesticide composition of the present invention is used for a control of epidemic, the application amount is usually 0.001 to 10 mg as an active ingredient per 1 m$^3$ in case of application for open space, and 0.001 to 100 mg as an active ingredient per 1 m$^2$ in case of application for plane surface. The emulsions, wettable powders and flowables are usually applied after dilution with water to have an active ingredient concentration of 0.01 to 100,000 ppm, while oil solutions, aerosols, smoking agents and poison baits are usually applied as such, and pesticide coils and electric pesticide mats are applied with emitting active ingredients by heating depending on their formulation form.

The pesticide composition of the present invention can also be used in admixture or combination with other insecticides, nematocides, acaricides, fungicides, herbicides, plant growth regulators, synergists, fertilizers, soil conditioners, animal feeds, and the like.

The active ingredients of such other insecticide and acaricide include, for example, pyrethroid compounds such as allethrin, tetramethrin, prallethrin, phenothrin, resmethrin, cyphenothrin, permethrin, cypermethrin, alpha-cypermethrin, zeta-cypermethrin, deltamethrin, tralomethrin, cyfluthrin, beta-cyfluthrin, cyhalothrin, lambda-cyhalothrin, flumethrin, imiprothrin, etofenprox, fenvalerate, esfenvalerate, fenpropathrin, silafluofen, bifenthrin, transfluthrin, flucythrinate, taufluvalinate, acrinathrin and tefluthrin; organophosphorus compounds such as dichlorvos, fenitrothion, cyanophos, profenofos, sulprofos, phenthoate, isoxathion, tetrachlorvinphos, fenthion, chlorpyriphos, diazinon, acephate, terbufos, phorate, chlorethoxyfos, fosthiazate, ethoprophos, cadusafos and methidathion; carbamate compounds such as propoxur, carbaryl, metoxadiazone, fenobucarb, methomyl, thiodicarb, alanycarb, benfuracarb, oxamyl, aldicarb and methiocarb; benzoylphenylurea compounds such as lufenuron, chlorfluazuron, hexaflumuron, diflubenzuron, triflumuron, teflubenzuron, flufenoxuron, fluazuron, novaluron and triazuron; juvenile hormone-like substances such as pyriproxyfen, methoprene, hydroprene and fenoxycarb; neonicotinoid compounds such as acetamiprid, nitenpyram, thiacloprid, thiamethoxam and dinotefuran; N-phenyl-pyrazole compounds such as acetoprole and ethiprole; benzoylhydrazine compounds such as tebufenozide, chromafenozide, methoxyfenozide and halofenozide; diafenthiuron; pymetrozine; flonicamid; triazamate; buprofezin; spinosad; emamectin benzoate; chlorfenapyr; indoxacarb MP; pyridalyl; cyromazine; fenpyroximate; tebufenpyrad; tolfenpyrad; pyridaben; pyrimidifen; fluacrypyrim; etoxazole; fenazaquin; acequinocyl; hexythiazox; clofentezine; fenbutatin oxide; dicofol, propargite; abamectin; milbemectin; amitraz; cartap; bensultap; thiocyclam; endosulfan; spirodiclofen; spiromesifen; and azadirachtin.

The present invention will be further illustrated by the following production examples, formulation examples, and test examples; however, the present invention is not limited to these examples. First, production examples of the present invention compounds are exemplified.

In the following production examples, the reference production examples, the data of $^1$H-NMR were measured in a solvent of deuterium chloroform with tetramethylsilane as the internal standard.

PRODUCTION EXAMPLE 1

200 mg of 3-methylsulfonyl-5-cyclohexyl-1,2,4-thiadiazole and 63 mg of 2-butyn-1-ol were dissolved in 2 g of N,N-dimethylformamide, 39 mg of sodium hydride (60% in oil) was added thereto under ice-cooling, and the reaction mixture was stirred for 30 minutes under ice-cooling and for 1 hour at room temperature. Then, the reaction mixture was added to saturated brine, and extracted with t-butyl methyl ether. The organic layer was concentrated under reduced pressure, and the residue obtained was subjected to silica gel column chromatography to give 79 mg of 5-cyclohexyl-3-(2-butynyloxy)-1,2,4-thiadiazole (hereinafter referred to as the present invention compound (1)).

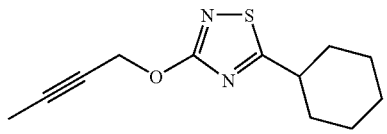

$^1$H-NMR: 4.97 (s, 2H), 2.99 (m, 1H), 2.15 (d, 2H), 1.88 (m, 5H), 1.73 (d, 1H), 1.56-1.21 (m, 5H)

PRODUCTION EXAMPLE 2

By using 75 mg of 2-pentyn-1-ol instead of 2-butyn-1-ol according to Production Example 1 was obtained 98 mg of 5-cyclohexyl-3-(2-pentynyloxy)-1,2,4-thiadiazole (hereinafter referred to as the present invention compound (2)).

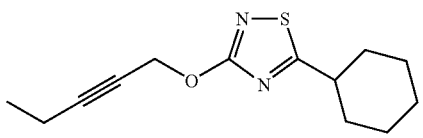

$^1$H-NMR: 5.00 (s, 2H), 2.99 (m, 1H), 2.24 (q, 2H), 2.13 (d, 2H), 1.85 (d, 2H), 2.74 (d, 1H), 1.56-1.24 (m, 5H), 1.14 (t, 3H)

PRODUCTION EXAMPLE 3

300 mg of 3-methylsulfonyl-5-cyclopentyl-1,2,4-thiadiazole and 99 mg of 2-butyn-1-ol were dissolved in 3 g of N,N-dimethylformamide, 62 mg of sodium hydride (60% in oil) was added thereto under ice-cooling, and the reaction mixture was stirred for 30 minutes under ice-cooling. Then, the reaction mixture was added to saturated brine, and extracted with t-butyl methyl ether. The organic layer was concentrated under reduced pressure, and the residue obtained was subjected to silica gel column chromatography to give 155 mg of 5-cyclopentyl-3-(2-butynyloxy)-1,2,4-thiadiazole (hereinafter referred to as the present invention compound (3)).

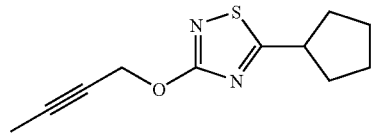

$^1$H-NMR: 4.97 (s, 2H), 3.43 (m, 1H), 2.19 (m, 2H), 1.89-1.61 (m, 9H)

PRODUCTION EXAMPLE 4

By using 119 mg of 2-pentyn-1-ol instead of 2-butyn-1-ol according to Production Example 3 was obtained 187 mg of 5-cyclopentyl-3-(2-pentynyloxy)-1,2,4-thiadiazole (hereinafter referred to as the present invention compound (4)).

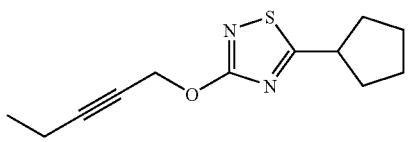

$^1$H-NMR: 5.00 (s, 2H), 3.45 (m, 1H), 2.23 (m, 4H), 1.87-1.68 (m, 6H), 1.13 (t, 3H)

PRODUCTION EXAMPLE 5

300 mg of 3-methylsulfonyl-5-(cyclohexyl)methyl-1,2,4-thiadiazole and 89 mg of 2-butyn-1-ol were dissolved in 2.5 g of N,N-dimethylformamide, 55 mg of sodium hydride (60% in oil) was added thereto, and the reaction mixture was stirred for 30 minutes under ice-cooling. Then, the reaction mixture was added to saturated brine, and extracted with t-butyl methyl ether. The organic layer was concentrated under reduced pressure, and the residue obtained was subjected to silica gel column chromatography to give 222 mg of 5-(cyclohexyl)methyl-3-(2-butynyloxy)-1,2,4-thiadiazole (hereinafter referred to as the present invention compound (5)).

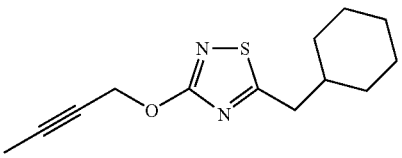

$^1$H-NMR: 4.98 (s, 2H), 2.89 (d, 2H), 1.87 (s, 3H), 1.82-1.62 (m, 6H), 1.31-0.98 (m, 5H)

PRODUCTION EXAMPLE 6

By using 106 mg of 2-pentyn-1-ol instead of 2-butyn-1-ol according to Production Example 5 was obtained 231 mg of 5-(cyclohexyl)methyl-3-(2-pentynyloxy)-1,2,4-thiadiazole (hereinafter referred to as the present invention compound (6)).

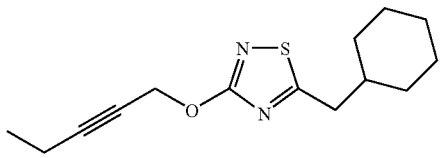

¹H-NMR: 4.99 (s, 2H), 2.86 (d, 2H), 2.24 (m, 2H), 1.84-1.65 (m, 6H), 1.30-0.96 (m, 8H)

PRODUCTION EXAMPLE 7

350 mg of 3-methylsulfonyl-5-(3-methylchclohexyl)-1,2,4-thiadiazole and 104 mg of 2-butyn-1-ol were dissolved in 3 ml of N,N-dimethylformamide, 75 mg of sodium hydride (60% in oil) was added thereto under ice-cooling, and the reaction mixture was stirred for 20 minutes under ice-cooling and for 20 minutes under room temperature. Then, the reaction mixture was added to saturated brine, and extracted with t-butyl methyl ether. The organic layer was concentrated under reduced pressure, and the residue obtained was subjected to silica gel column chromatography to give 280 mg of 5-(3-methylcyclohexyl)-3-(2-butynyloxy)-1,2,4-thiadiazole (hereinafter referred to as the present invention compound (7)).

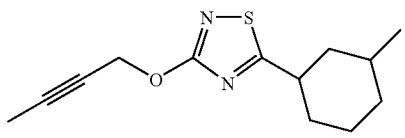

¹H-NMR: 4.97 (s, 2H), 3.00 (m, 0.7H), 2.91 (m, 0.3H), 2.21-1.95 (m, 3H), 1.95-1.78 (m, 4H), 1.78-1.68 (d, 1H), 1.68-1.27 (m, 3H), 1.27-1.01 (m, 1H), H), 0.94 (m, 3H)

PRODUCTION EXAMPLE 8

By using 125 mg of 2-pentyn-1-ol instead of 2-butyn-1-ol according to Production Example 7 was obtained 270 mg of 5-(3-methylcyclohexyl)-3-(2-pentynyloxy)-1,2,4-thiadiazole (hereinafter referred to as the present invention compound (8)).

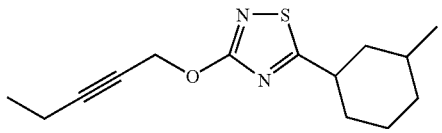

¹H-NMR: 4.99 (s, 2H), 3.00 (m, 0.7H), 2.90 (m, 0.3H), 2.23 (m, 2H), 2.14 (m, 2H), 2.06-1.68 (m, 3H), 1.68-1.28 (m, 3H), 1.13 (m, 4H), 0.95 (m, 3H)

PRODUCTION EXAMPLE 9

300 mg of 3-methylsulfonyl-5-(2-norbornyl)-1,2,4-thiadiazole and 107 mg of 2-pentyn-1-ol were dissolved in 2.5 g of N,N-dimethylformamide, 60 mg of sodium hydride (60% in oil) was added thereto under ice-cooling, and the reaction mixture was stirred for 30 minutes under ice-cooling and for 1 hour under room temperature. Then, the reaction mixture was added to saturated brine, and extracted with t-butyl methyl ether. The organic layer was concentrated under reduced pressure, and the residue obtained was subjected to silica gel column chromatography to give 5-(2-norbornyl)-3-(2-butynyloxy)-1,2,4-thiadiazole. 150 mg of the exo-isomer having low polarity (hereinafter referred to as the present invention compound (9-1)) and 50 mg of the endo-isomer having high polarity (hereinafter referred to as the present invention compound (9-2)) were obtained by using hexane-ethyl acetate system as a carrier solvent.

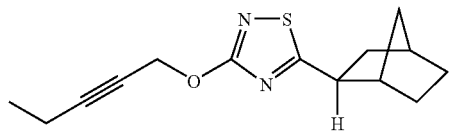

¹H-NMR: 4.99 (s, 2H), 3.05 (t, 1H), 2.50 (s, 1H), 2.40 (s, 1H), 2.24 (m, 2H), 1.83 (d, 2H), 1.68-1.53 (m, 3H), 1.39 (m, 1H), 1.27 (m, 2H), 1.14 (t, 3H)

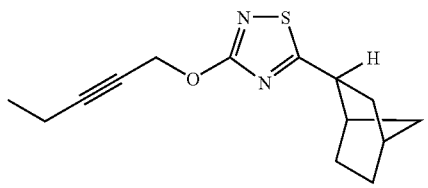

¹H-NMR: 4.99 (s, 2H), 3.45 (m, 1H), 2.66 (m, 1H), 2.38 (m, 1H), 2.23 (m, 2H), 2.11 (m, 1H), 1.55 (m, 2H), 1.45 (m, 2H), 1.39 (m, 1H), 1.26 (m, 2H), 1.16 (t, 3H)

PRODUCTION EXAMPLE 10

160 mg of 3-methylsulfonyl-5-(2-methylcyclohexyl)-1,2,4-thiadiazole and 52 mg of 2-butyn-1-ol were dissolved in 1.5 ml of N,N-dimethylformamide, 32 mg of sodium hydride (60% in oil) was added thereto under ice-cooling, and the reaction mixture was stirred for 1 hour under ice-cooling and for 12 hours at room temperature. Then, the reaction mixture was added to saturated brine, and extracted with t-butyl methyl ether. The organic layer was concentrated under reduced pressure, and the residue obtained was subjected to silica gel column chromatography to give 39 mg of 5-(2-methylcyclohexyl)-3-(2-butynyloxy)-1,2,4-thiadiazole (hereinafter referred to as the present invention compound (10)).

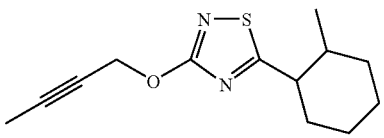

¹H-NMR: 4.98 (s, 2H), 3.05-2.93 (m, 1H), 2.16 (m, 2H), 1.88-1.65, 1.65-0.84 (m, 15H)

mass: m/e=250(M⁺)

PRODUCTION EXAMPLE 11

By using 62 mg of 2-pentyn-1-ol instead of 2-butyn-1-ol according to Production Example 10 was obtained 58 mg of 5-(2-methylcyclohexyl)-3-(2-pentynyloxy)-1,2,4-thiadiazole (hereinafter referred to as the present invention compound (11)).

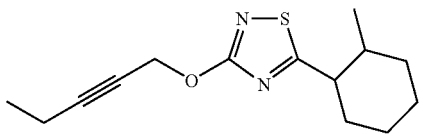

¹H-NMR: 5.05 (s, 2H), 3.04-2.93 (m, 1H), 2.30-0.84 (m, 17H)
mass: m/e=264(M⁺)

PRODUCTION EXAMPLE 12

400 mg of 3-methylsulfonyl-5-(4-methylcyclohexyl)-1,2,4-thiadiazole and 129 mg of 2-butyn-1-ol were dissolved in 3 ml of N,N-dimethylformamide, 80 mg of sodium hydride (60% in oil) was added thereto under ice-cooling, and the reaction mixture was stirred for 1 hour under ice-cooling and for 12 hours at room temperature. Then, the reaction mixture was added to saturated brine, and extracted with t-butyl methyl ether. The organic layer was concentrated under reduced pressure, and the residue obtained was subjected to silica gel column chromatography to give 258 mg of 5-(4-methylcyclohexyl)-3-(2-butynyloxy)-1,2,4-thiadiazole (hereinafter referred to as the present invention compound (12)).

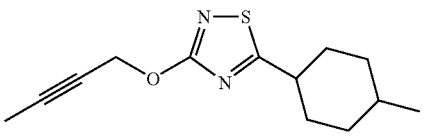

¹H-NMR: 4.98 (s, 2H), 3.02-2.85 (m, 1H), 2.15, 1.87-0.93 (m, 17H)
mass: m/e=250 (M⁺)

PRODUCTION EXAMPLE 13

By using 155 mg of 2-pentyn-1-ol instead of 2-butyn-1-ol according to Production Example 12 was obtained 282 mg of 5-(4-methylcyclohexyl)-3-(2-pentynyloxy)-1,2,4-thiadiazole (hereinafter referred to as the present invention compound (13)).

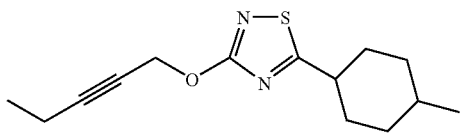

¹H-NMR: 5.00 (s, 2H), 3.05-2.86 (m, 1H), 2.23, 2.13, 1.83, 1.83-1.20, 1.20-1.00, 1.00-0.89 (m, 17H)
mass: m/e=264 (M⁺)

PRODUCTION EXAMPLE 14

170 mg of 3-methylsulfonyl-5-(3-ethylcyclohexyl)-1,2,4-thiadiazole and 52 mg of 2-butyn-1-ol were dissolved in 1.5 ml of N,N-dimethylformamide, 32 mg of sodium hydride (60% in oil) was added thereto under ice-cooling, and the reaction mixture was stirred for 1 hour under ice-cooling and for 12 hours under room temperature. Then, the reaction mixture was added to saturated brine, and extracted with t-butyl methyl ether. The organic layer was concentrated under reduced pressure, and the residue obtained was subjected to silica gel column chromatography to give 80 mg of 5-(3-ethylcyclohexyl)-3-(2-butynyloxy)-1,2,4-thiadiazole (hereinafter referred to as the present invention compound (14)).

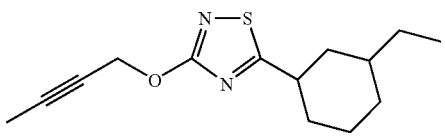

¹H-NMR: 4.97 (s, 2H), 3.03-2.90 (m, 1H), 2.16 (m, 2H), 1.95-1.78 (m, 6H), 1.48-1.25 (m, 5H), 1.13 (m, 1H), 0.90 (m, 3H)
mass: m/e=264 (M+)

PRODUCTION EXAMPLE 15

By using 63 mg of 2-pentyn-1-ol instead of 2-butyn-1-ol according to Production Example 14 was obtained 83 mg of 5-(3-ethylcyclohexyl)-3-(2-pentynyloxy)-1,2,4-thiadiazole (hereinafter referred to as the present invention compound (15)).

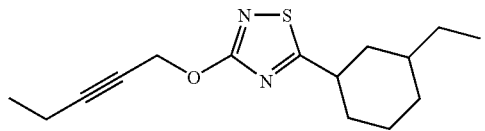

¹H-NMR: 4.99 (s, 2H), 3.03-2.93 (m, 1H), 2.28-2.13, 1.93-1.79, 1.46-1.23, 1.13, 0.89 (m, 19H)

Productions of intermediates of the present invention compounds are here exemplified as Reference Production Example.

REFERENCE PRODUCTION EXAMPLE 1

500 mg of 5-chloro-3-methylthio-1,2,4-thiadiazole and 122 mg of {1,1'-bis(diphenylphosphino)ferrocene} dichloro palladium(II) dichloromethane complex were dissolved in 6 ml of tetrahydrofuran under nitrogen atmosphere, 6.58 ml of solution of cyclohexyl zinc bromide in tetrahydrofuran (0.5 mol/l) was added thereto under ice-cooling taking for about 5 minutes, and the reaction mixture was stirred for 16 hours at room temperature. Then, the reaction mixture was concentrated, and the residue subjected to silica gel column chromatography to give 370 mg of 3-methylthio-5-cyclohexyl-1,2,4-thiadiazole.

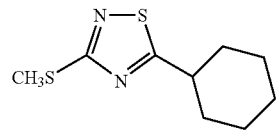

¹H-NMR: 3.05 (m, 1H), 3.68 (s, 3H), 2.13 (d, 2H), 1.86 (d, 2H), 1.74 (d, 1H), 1.50-1.24 (m, 5H)

370 mg of 3-methylthio-5-cyclohexyl-1,2,4-thiadiazole was dissolved in 8 ml of chloroform, 1.12 g of 3-chloroperoxybenzoic acid (content>65%) was added thereto, and the reaction mixture was stirred for 7 hours under ice-cooling. Then, the reaction mixture was added to saturated sodium hydrogensulfite aqueous solution, and separated. The organic layer was washed with sodium hydrogencarbonate aqueous solution, dried over anhydrous sodium sulfate, concentrated to give 444 mg of 3-methylsulfonyl-5-cyclohexyl-1,2,4-thiadiazole.

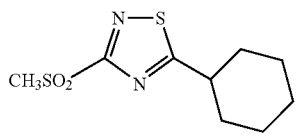

$^1$H-NMR: 3.38 (s, 3H), 2.19 (m, 1H), 2.21 (d, 2H), 1.88 (d, 2H), 1.78 (d, 1H), 1.54-1.24 (m, 5H)

REFERENCE PRODUCTION EXAMPLE 2

1.00 g of 5-chloro-3-methylthio-1,2,4-thiadiazole and 244 mg of {1,1'-bis(diphenylphosphino)ferrocene} dichloro palladium(II) dichloromethane complex were dissolved in 12 ml of tetrahydrofuran under nitrogen atmosphere, 13.2 ml of solution of cyclopentyl zinc bromide in tetrahydrofuran (0.5 mol/l) was added thereto under ice-cooling taking for about 15 minutes, and the reaction mixture was stirred for 13 hours at room temperature. Then, the reaction mixture was concentrated, and the residue subjected to silica gel column chromatography to give 710 mg of 3-methylthio-5-cyclopentyl-1,2,4-thiadiazole.

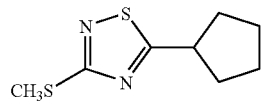

H-NMR: 3.49 (m, 1H), 2.67 (s, 3H), 2.22-2.19 (m, 2H), 1.83-1.72 (m, 6H)

710 mg of 3-methylthio-5-cyclopentyl-1,2,4-thiadiazole was dissolved in 15 ml of chloroform, 1.89 g of 3-chloroperoxybenzoic acid (content>65%) was added thereto, and the reaction mixture was stirred for 30 minutes under ice-cooling and for 3.5 hours at room temperature. Then, the reaction mixture was added to saturated sodium hydrogensulfite aqueous solution, and separated. The organic layer was washed with sodium hydrogencarbonate aqueous solution, dried over anhydrous sodium sulfate, concentrated to give 804 mg of 3-methylsulfonyl-5-cyclopentyl-1,2,4-thiadiazole.

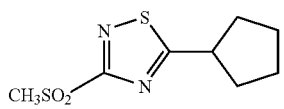

$^1$H-NMR: 3.61 (m, 1H), 3.37 (s, 3H), 2.31-2.26 (m, 2H), 1.88-1.77 (m, 6H)

REFERENCE PRODUCTION EXAMPLE 3

1.00 g of 5-chloro-3-methylthio-1,2,4-thiadiazole and 244 mg of {1,1'-bis(diphenylphosphino)ferrocene} dichloro palladium(II) dichloromethane complex were dissolved in 12 ml of tetrahydrofuran under nitrogen atmosphere, 13.2 ml of solution of (cyclohexyl)methyl zinc bromide in tetrahydrofuran (0.5 mol/l) was added thereto under ice-cooling taking for about 10 minutes, and the reaction mixture was stirred for 30 minutes under ice-cooling and for 8 hours at room temperature. Then, the reaction mixture was concentrated, and the residue subjected to silica gel column chromatography to give 1.29 g of 3-methylthio-5-(cyclohexyl)methyl-1,2,4-thiadiazole.

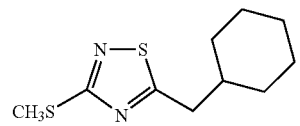

$^1$H-NMR: 2.93 (d, 2H), 2.67 (s, 3H), 1.77-1.65 (m, 6H), 1.27-1.01 (m, 5H)

1.2 g of 3-methylthio-5-(cyclohexyl)methyl-1,2,4-thiadiazole was dissolved in 20 ml of chloroform, 2.78 g of 3-chloroperoxybenzoic acid (content>65%) was added thereto, and the reaction mixture was stirred for 1 hour under ice-cooling and for 16 hours at room temperature. Then, the reaction mixture was added to saturated sodium hydrogensulfite aqueous solution, and separated. The organic layer was washed with sodium hydrogencarbonate aqueous solution, dried over anhydrous sodium sulfate, concentrated to give 1.4 g of 3-methylsulfonyl-5-(cyclohexyl)methyl-1,2,4-thiadiazole.

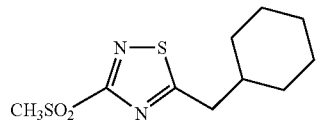

$^1$H-NMR: 3.38 (s, 3H), 3.06 (d, 2H), 1.88-1.65 (m, 6H), 1.29-1.05 (m, 5H)

REFERENCE PRODUCTION EXAMPLE 4

1.31 g of zinc foil (99.998%) and 190 mg of 1,2-dibromoethane was added into 2 ml of tetrahydrofurane under nitrogen atmosphere and the mixture was heated in an oil bath at 65° C. for 1 minute. After cooling to room temperature, 0.1 ml of trimethylsilyl chloride, 2.14 g of 3-methylcyclohexyl iodide and 10 ml of tetrahydrofuran were added to the mixture, and the mixture was exposed to ultrasonic wave in a water bath for 4 hours. Further, 1.31 g of 5-chloro-3-methylthio-1,2,4-thiadiazole, 390 mg of {1,1'-bis(diphenylphosphino)ferrocene} dichloro palladium(II) dichloromethane complex and 10 ml of tetrahydrofuran were added in the mixture, and the reaction mixture was stirred for 3.5 days at room temperature. The reaction mixture was concentrated, and the residue subjected to silica gel column chromatography to give 790 mg of 5-(3-methylcyclohexyl)-3-methylthio-1,2,4-thiadiazole.

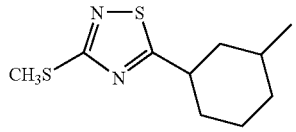

¹H-NMR: 3.12-2.91 (m, 1H), 2.68 (s, 3H), 2.16 (m, 2H), 1.91-1.72 (m, 2H), 1.60-1.34 (m, 4H), 1.23-1.02 (m, 1H), 0.97 (t, 3H)

700 mg of 5-(3-methylcyclohexyl)-3-methylthio-1,2,4-thiadiazole was dissolved in 6 ml of chloroform, 1.73 g of 3-chloroperoxybenzoic acid (content>65%) was added thereto, and the reaction mixture was stirred for 30 minutes under ice-cooling and for 1.5 hours under room temperature. Then, the reaction mixture was added to saturated sodium hydrogensulfite aqueous solution, and separated. The organic layer was washed with sodium hydrogencarbonate aqueous solution, dried over anhydrous sodium sulfate, concentrated to give 784 mg of 3-methylsulfonyl-5-(3-methylcyclohexyl)-1,2,4-thiadiazole.

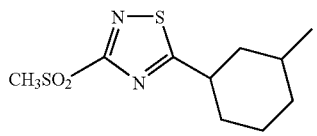

¹H-NMR: 3.38 (s, 3H), 3.24-3.02 (m, 1H), 2.24 (m, 2H), 1.96-1.74 (m, 2H), 1.67-1.38 (m, 4H), 1.28-1.06 (m, 1H), 0.98 (t, 3H)

REFERENCE PRODUCTION EXAMPLE 5

1.67 g of 5-chloro-3-methylthio-1,2,4-thiadiazole and 245 mg of {1,1'-bis(diphenylphosphino)ferrocene} dichloro palladium(II) dichloromethane complex were dissolved in 10 ml of tetrahydrofuran under nitrogen atmosphere, 21.2 ml of solution of exo-2-norbornyl zinc chloride in tetrahydrofuran (0.5 mol/l) was added thereto at room temperature, and the reaction mixture was stirred for 1 day at room temperature. Then, the reaction mixture was concentrated, and the residue subjected to silica gel column chromatography to give 1.0 g of 5-(2-norbornyl)-3-methylthio-1,2,4-thiadiazole.

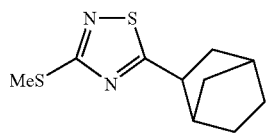

¹H-NMR: 3.50 (m, 0.3H), 3.15 (m, 0.7H), 2.68 (s), 2.67 (s, 3H), 2.51 (br), 2.42 (br), 2.18 (m), 1.95-1.79 (m), 1.70-1.33 (m), 1.28 (m, 10H)

1.0 g of 5-(2-norbornyl)-3-methylthio-1,2,4-thiadiazole was dissolved in 9 ml of chloroform, 3.67 g of 3-chloroperoxybenzoic acid (content>65%) was added thereto, and the reaction mixture was stirred for 30 minutes under ice-cooling and for 1 day at room temperature. Then, the reaction mixture was added to saturated sodium hydrogensulfite aqueous solution, and separated. The organic layer was washed with sodium hydrogencarbonate aqueous solution, dried over anhydrous sodium sulfate, concentrated to give 833 mg of 5-(2-norbornyl)-3-methylsulfonyl-1,2,4-thiadiazole.

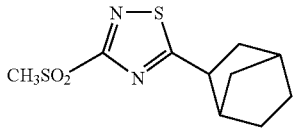

¹H-NMR: 3.63 (m, 0.3H), 3.38 (s, 0.3H), 3.37 (s, 0.7), 3.25 (m, 0.7H), 2.75 (m, 0.3H), 2.56 (br), 2.48 (br), 2.23 (m), 1.98 (m, 2H), 1.87 (m), 1.75-1.38 (m), 1.32 (m), 1.16 (m, 10H)

REFERENCE PRODUCTION EXAMPLE 6

583 mg of zinc powder and 83 mg of 1,2-dibromoethane was added into 9 ml of tetrahydrofurane under nitrogen atmosphere and the mixture was refluxed for 1 minute. After cooling to room temperature, 49 mg of trimethylsilyl chloride and 3.0 g of 2-methylcyclohexyl iodide were added to the mixture, and the mixture was stirred for 6 hours at room temperature. Further, 1.49 g of 5-chloro-3-methylthio-1,2,4-thiadiazole and 109 mg of {1,1'-bis(diphenylphosphino)ferrocene} dichloro palladium(II) dichloromethane complex were added in the mixture, and the reaction mixture was stirred for 15 hours at room temperature and refluxed for 5 hours. The reaction mixture was concentrated, and the residue subjected to silica gel column chromatography to give 564 mg of 5-(2-methylcyclohexyl)-3-methylthio-1,2,4-thiadiazole.

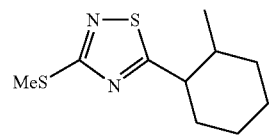

¹H-NMR: 3.12-3.02, 2.95 (m, 1H), 2.68 (s, 3H), 2.14 (m, 2H), 1.90-1.02 (m), 0.96 (m), 0.82 (m, 10H)

500 mg of 5-(2-methylcyclohexyl)-3-methylthio-1,2,4-thiadiazole was dissolved in 6.5 ml of chloroform, 1.62 g of 3-chloroperoxybenzoic acid (content>65%) was added thereto taking for 20 minutes, and the reaction mixture was stirred for 30 minutes under ice-cooling and for 1.5 hours under room temperature. Then, the reaction mixture was added to saturated sodium hydrogensulfite aqueous solution, and separated. The organic layer was washed with sodium hydrogencarbonate aqueous solution, dried over anhydrous sodium sulfate, concentrated to give 466 mg of 3-methylsulfonyl-5-(2-methylcyclohexyl)-1,2,4-thiadiazole.

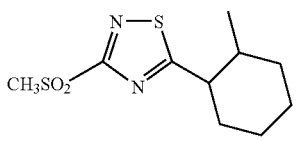

¹H-NMR: 3.38 (m, 3H), 3.19 (m, 1H), 2.22 (br), 1.96-1.03 (m), 0.97 (m), 0.83 (m, 12H)

REFERENCE PRODUCTION EXAMPLE 7

By using 3.0 g of 4-methylcyclohexyl iodide instead of 2-methylcyclohexyl according to Reference Production Example 6 was obtained 1.03 g of 5-(4-methylcyclohexyl)-3-methylthio-1,2,4-thiadiazole.

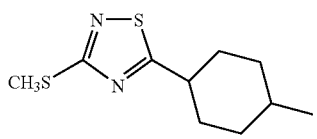

$^1$H-NMR: 3.12-2.92 (m, 1H), 2.69 (s, 3H), 2.16 (m, 2H), 1.85 (m, 2H), 1.80-1.03 (m), 0.97 (m, 8H)

900 mg of 5-(4-methylcyclohexyl)-3-methylthio-1,2,4-thiadiazole was dissolved in 8 ml of chloroform, 2.22 g of 3-chloroperoxybenzoic acid (content>65%) was added thereto taking for 20 minutes, and the reaction mixture was stirred for 4 hours at room temperature. Then, the reaction mixture was added to saturated sodium hydrogensulfite aqueous solution, and separated. The organic layer was washed with sodium hydrogencarbonate aqueous solution, dried over anhydrous sodium sulfate, concentrated to give 1.11 g of 3-methylsulfonyl-5-(4-methylcyclohexyl)-1,2,4-thiadiazole.

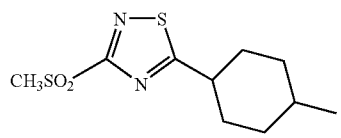

$^1$H-NMR: 3.39 (s, 3H), 3.27-3.05 (m, 1H), 2.26 (m), 2.14-1.06 (m), 0.97 (m, 12H)

REFERENCE PRODUCTION EXAMPLE 8

439 mg of zinc powder and 63 mg of 1,2-dibromoethane was added into 7 ml of tetrahydrofurane under nitrogen atmosphere and the mixture was refluxed for 1 minute. After cooling to room temperature, 36 mg of trimethylsilyl chloride and 3.0 g of 3-ethylcyclohexyl iodide were added to the mixture, and the mixture was stirred for 6 hours at room temperature. Further, 561 mg of 5-chloro-3-methylthio-1,2,4-thiadiazole and 137 mg of {1,1'-bis(diphenylphosphino)ferrocene} dichloro palladium(II) dichloromethane complex were added in the mixture, and the reaction mixture was refluxed for 17 hours. The reaction mixture was concentrated, and the residue subjected to silica gel column chromatography to give 384 mg of 5-(3-ethylcyclohexyl)-3-methylthio-1,2,4-thiadiazole.

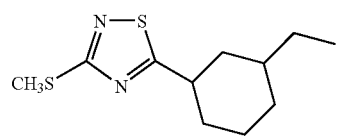

$^1$H-NMR: 3.06 (m, 1H), 2.68 (s, 3H), 2.22-2.14 (m, 2H), 1.92-1.80 (m, 2H), 1.45-1.09, 0.91 (m, 10H)

320 mg of 5-(3-ethylcyclohexyl)-3-methylthio-1,2,4-thiadiazole was dissolved in 2.5 ml of chloroform, 738 mg of 3-chloroperoxybenzoic acid (content>65%) was added thereto taking for 20 minutes, and the reaction mixture was stirred for 20 minutes at room temperature. Then, the reaction mixture was added to saturated sodium hydrogensulfite aqueous solution, and separated. The organic layer was washed with sodium hydrogencarbonate aqueous solution, dried over anhydrous sodium sulfate, concentrated to give 380 mg of 3-methylsulfonyl-5-(3-ethylcyclohexyl)-1,2,4-thiadiazole.

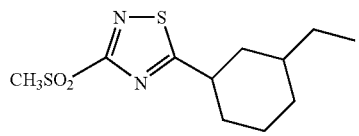

$^1$H-NMR: 3.37 (s, 3H), 3.23-3.09 (m, 1H), 2.26 (m), 1.95 (m), 1.85 (m), 1.58-1.02 (m, 11H), 0.92 (t, 3H)

Formulation Examples are exemplified below. In addition, "part" means a part by weight. The present invention compounds are designated by their compound numbers shown above.

FORMULATION EXAMPLE 1

9 Parts of each of the present invention compounds (1) to (15) are dissolved in 37.5 parts of xylene and 37.5 parts of dimethylformamide, and 10 parts of polyoxyethylene styryl phenyl ether and 6 parts of calcium dodecylbenzenesulfonate are added thereto, followed by well stirring and mixing, to give an emulsion for each compound.

FORMULATION EXAMPLE 2

9 Parts of each of the present compounds (1) to (15) is added to a mixture containing 4 parts of sodium laurylsulfate, 2 parts of calcium lignin sulfonate, 20 parts of synthetic hydrated silicone oxide fine powder, and 65 parts of diatomaceous earth, followed by well stirring and mixing, to give a wettable powder for each compound.

FORMULATION EXAMPLE 3

To 3 parts of each of the present invention compounds (1) to (15) are added 5 parts of synthetic hydrated silicon oxide fine powder, 5 parts of sodium dodecylbenzenesulfonate, 30 parts of bentonite and 57 parts of clay, followed by well stirring and mixing. Then an appropriate amount of water is added to this mixture, followed by further stirring, granulating with a granulator and air drying, to give a granule for each compound.

FORMULATION EXAMPLE 4

4.5 Parts of each of the present invention compounds (1) to (15), 1 part of synthetic hydrated silicon oxide fine powder, 1 part of Doriresu B (Sankyo Co., Ltd.) as a flocculant and 7 parts of clay are well mixed with a mortar, followed by stirring and mixing with a juice mixer. To the resulting mixture is added 86.5 parts of cut clay, followed by well stirring and mixing, to give a powder for each compound.

FORMULATION EXAMPLE 5

10 Parts of each of the present invention compounds (1) to (15), 35 parts of white carbon containing 50 parts of polyoxyethylene alkyl ether sulfate ammonium salt and 55 parts of water are mixed and pulverized by the wet grinding method to give a formulation for each compound.

FORMULATION EXAMPLE 6

0.5 Parts of each of the present invention compounds (1) to (15) are dissolved in 10 parts of dichloromethane, and the resulting solution is mixed with 89.5 parts of Iso-Par M (isoparaffine: registered trade name for EXXON CHEMICAL LTD) to give an oil solution.

FORMULATION EXAMPLE 7

0.1 Parts of each of the present invention compounds (1) to (15) and 49.9 parts of NEO-CHIOZOL (CHUO KASEI Co., LTD) are charged into aerosol can, and aerosol valve is fixed to the can. Then 25 parts of dimethyl ether and 25 parts of LPG are filled in the can, followed by shaking and fitting an actuator on it, to give an oil aerosol.

FORMULATION EXAMPLE 8

0.6 Parts of each of the present invention compounds (1) to (15), 0.01 parts of BHT, 5 parts of xylene, 3.39 parts of deodorized kerosene and 1 part of emulsifier [Atmos 300 (registered trade name for ATMOS CHEMICAL LTD)] are mixed and dissolved. The resulting solution and 50 parts of distilled water are charged into aerosol container, and a valve is fixed to the container. 40 Parts of propellant (LPG) are charged under pressure through the valve to give an aqueous aerosol.

The following test example will demonstrate that the present invention compounds is useful as active ingredient of an arthropod pests controlling composition.

TEXT EXAMPLE

The formulation of each of the present invention compounds (1) to (15) according to Formulation Example 5 was diluted with water so that the active ingredient concentration came to 500 ppm to prepare a spray solution.

A polyethylene cup was seeded with cucumber and a plant was grown until the first true leaf was developed, on which about twenty *Aphis gossypii* (cotton aphid) are allowed to be parasitic. On the next day, the above spray solution was applied at a ratio of 20 ml/cup to the cucumber plant. On the sixth day after the application, the number of *Aphis gossypii* was examined.

As a result, in the treatment with each of the present invention compounds (1) to (15), the number of parasitic *Aphis gossypii* was not greater than 3.

INDUSTRIAL APPLICABILITY

Arthropod pests such as insect pests, acarine pests and the like can be effectively controlled by the present invention.

The invention claimed is:

1. A 1,2,4-thiadiazole compound represented by the formula (1):

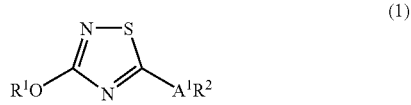

wherein, $R^1$ represents $C_3$-$C_7$ alkynyl optionally substituted with a halogen atom;

$R^2$ represents $C_3$-$C_8$ cycloalkyl, $C_5$-$C_8$ cycloalkenyl or $C_7$-$C_{11}$ bicycloalkyl, wherein the $C_3$-$C_8$ cycloalkyl, the $C_5$-$C_8$ cycloalkenyl and the $C_7$-$C_{11}$ bicycloalkyl is optionally substituted with one or more substituents selected from the group consisting of $C_1$-$C_4$ alkyl, a halogen atom and trifluoromethyl; and $A^1$ represents a single bond, $C_1$-$C_2$ alkylene or $C_2$-$C_3$ alkylidene.

2. The 1,2,4-thiadiazole compound according to claim 1, wherein $R^2$ is $C_3$-$C_8$ cycloalkyl optionally substituted with $C_1$-$C_4$ alkyl.

3. The 1,2,4-thiadiazole compound according to claim 2, wherein $A^1$ is a single bond.

4. The 1,2,4-thiadiazole compound according to claim 2, wherein $A^1$ is $C_1$-$C_2$ alkylene.

5. The 1,2,4-thiadiazole compound according to claim 2, wherein $R^1$ is 2-butynyl or 2-pentynyl.

6. The 1,2,4-thiadiazole compound according to claim 1, wherein $A^1$ is a single bond.

7. The 1,2,4-thiadiazole compound according to claim 1, wherein $A^1$ is $C_1$-$C_2$ alkylene.

8. The 1,2,4-thiadiazole compound according to claim 1, wherein $R^1$ is 2-butynyl or 2-pentynyl.

9. An arthropod controlling composition comprising the 1,2,4-thiadiazole compound according to claim 1 and an inert carrier.

10. A method for controlling arthropod pests comprising applying an effective dose of the 1,2,4-thiadiazole compound according to claim 1 to the arthropod pests or habitat of the arthropod pests.

11. An insect controlling composition comprising the 1,2,4-thiadiazole compound according to claim 1 and an inert carrier.

12. A method for controlling insect pests comprising applying an effective dose of the 1,2,4-thiadiazole compound according to claim 1 to the insect pests or habitat of the insect pests.

13. The method according to claim 12, wherein the insect pests are selected from the group consisting of Hemiptera, Lepidoptera, Diptera, Coleoptera, Thysanoptera, Hymenoptera, Dictyoptera, Orthoptera, Anoplura, and Isoptera.

14. An acarine controlling composition comprising the 1,2,4-thiadiazole compound according to claim 1 and an inert carrier.

15. The method according to claim 14, wherein the acarine pests are acarina.

16. A method for controlling acarine pests comprising applying an effective dose of the 1,2,4-thiadiazole compound according to claim 1 to the acarine pests or habitat of the acarine pests.

* * * * *